United States Patent
Kuo et al.

(10) Patent No.: US 10,358,585 B2
(45) Date of Patent: Jul. 23, 2019

(54) POLYPHENYLENE ETHER OLIGOMER AND HIGH-FREQUENCY COPPER CLAD LAMINATE

(71) Applicant: INDUSTRIAL TECHNOLOGY RESEARCH INSTITUTE, Hsinchu (TW)

(72) Inventors: Cheng-Po Kuo, Taipei (TW); Po-Ju Chen, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 370 days.

(21) Appl. No.: 15/386,669

(22) Filed: Dec. 21, 2016

(65) Prior Publication Data

US 2017/0174957 A1     Jun. 22, 2017

Related U.S. Application Data

(60) Provisional application No. 62/270,843, filed on Dec. 22, 2015.

(51) Int. Cl.

| | |
|---|---|
| C09J 163/00 | (2006.01) |
| C07C 69/54 | (2006.01) |
| C07C 43/285 | (2006.01) |
| C07D 303/24 | (2006.01) |
| C09J 4/00 | (2006.01) |
| B32B 7/12 | (2006.01) |
| B32B 15/04 | (2006.01) |
| B32B 27/06 | (2006.01) |
| C07C 43/295 | (2006.01) |

(Continued)

(52) U.S. Cl.
CPC ............ *C09J 163/00* (2013.01); *B32B 7/12* (2013.01); *B32B 15/04* (2013.01); *B32B 27/06* (2013.01); *C07C 43/285* (2013.01); *C07C 43/295* (2013.01); *C07C 69/54* (2013.01); *C07D 303/24* (2013.01); *C08G 59/063* (2013.01); *C08G 65/38* (2013.01); *C08G 65/4093* (2013.01); *C08G 65/485* (2013.01); *C09J 4/00* (2013.01); *C09J 171/12* (2013.01); *C07C 2603/68* (2017.05)

(58) Field of Classification Search
USPC ........................................................ 528/219
See application file for complete search history.

(56) References Cited

U.S. PATENT DOCUMENTS

| | | |
|---|---|---|
| 6,689,920 B2 | 2/2004 | Ishii et al. |
| 7,329,708 B2 | 2/2008 | Birsak et al. |

(Continued)

FOREIGN PATENT DOCUMENTS

| | | |
|---|---|---|
| EP | 0417510 A1 | 3/1991 |
| JP | 2002-53646 A | 2/2002 |

(Continued)

OTHER PUBLICATIONS

Chinese Office Action and Search Report for Chinese Application No. 201611192062.2, dated Sep. 11, 2018.

(Continued)

*Primary Examiner* — Terressa Boykin
(74) *Attorney, Agent, or Firm* — Birch, Stewart, Kolasch & Birch, LLP

(57) ABSTRACT

A polyphenylene ether oligomer and a polyphenylene ether oligomer are provided. The polyphenylene ether oligomer has a structure represented by Formula (I):

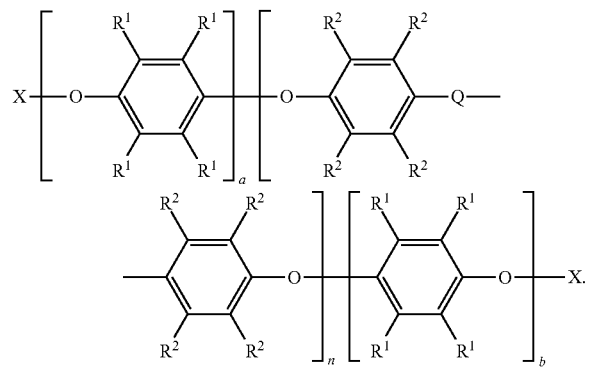

Formula (I)

wherein each $R^1$ can be independently hydrogen, $C_{1-6}$ alkyl group, or phenyl group; each $R^2$ can be independently hydrogen, $C_{1-6}$ alkyl group, or phenyl group; a:(a+b) is from 0.05:1 to 1:1; n:(a+b) is from 0.05:1 to 5:1; Q can be

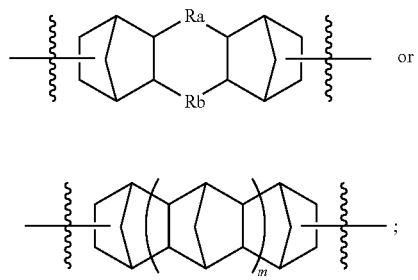

m can be 0 or an integer from 1 to 4; Ra can be $C_{1-6}$ alkylene group; Rb can be $C_{1-6}$ alkylene group; each X is independently hydrogen, acryloyl group, allyl group, vinylbenzyl group, epoxypropyl group, methacryloyl group, propargyl group, or cyanol group; and wherein the polyphenylene ether oligomer can have a number average molecular weight from 400 to 2,000.

10 Claims, No Drawings

(51) Int. Cl.
*C08G 59/06* (2006.01)
*C08G 65/38* (2006.01)
*C08G 65/40* (2006.01)
*C08G 65/48* (2006.01)
*C09J 171/12* (2006.01)

(56) References Cited

U.S. PATENT DOCUMENTS

| | | |
|---|---|---|
| 7,541,421 B2 | 6/2009 | Carrillo et al. |
| 7,595,361 B2 | 9/2009 | Guerin et al. |
| 7,595,367 B2 | 9/2009 | Carrillo et al. |
| 7,671,167 B2 | 3/2010 | Carrillo et al. |
| 7,781,537 B2 | 8/2010 | Birsak et al. |
| 7,847,032 B2 | 12/2010 | Guo et al. |
| 8,017,697 B2 | 9/2011 | Carrillo et al. |
| 8,669,332 B2 | 3/2014 | Carrillo et al. |
| 9,080,046 B2 | 7/2015 | Peters |
| 2008/0085989 A1 | 4/2008 | Yeager et al. |
| 2008/0269427 A1 | 10/2008 | Ishii et al. |
| 2009/0247724 A1 | 10/2009 | Carrillo et al. |
| 2011/0152420 A1 | 6/2011 | Elkovitch et al. |

FOREIGN PATENT DOCUMENTS

| | | |
|---|---|---|
| JP | 2003-252833 A | 9/2003 |
| JP | 2004-59645 A | 2/2004 |
| TW | 572882 B | 1/2004 |
| TW | 591054 B | 6/2004 |
| TW | I319769 B | 1/2010 |

OTHER PUBLICATIONS

Hwang et al., "Low dielectric epoxy resins from dicyclopentadiene-containing poly(phenylene oxide) novolac cured with dicyclopentadiene containing epoxy," Elsevier, Reactive and Functional Polymers, vol. 68, 2008 (available online May 10, 2008), pp. 1185-1193.
Taiwanese Notice of Allowance for Appl. No. 105142422 dated Feb. 26, 2018.
Hay, "Poly(phenylene oxide)s and poly(arylene ether)s derived from 2,6-diarylphenols," Progress in Polymer Science, vol. 24, 1999, pp. 45-80.
Tanaka et al., "Anion Conductive Block Poly(arylene ether)s: Synthesis, Properties, and Application in Alkaline Fuel Cells," Journal of the American Chemical Society, vol. 133, Jun. 9, 2011, pp. 10646-10654.

POLYPHENYLENE ETHER OLIGOMER AND HIGH-FREQUENCY COPPER CLAD LAMINATE

CROSS REFERENCE TO RELATED APPLICATIONS

This application claims the benefit of U.S. Provisional Application No. 62/270,843, filed on Dec. 22, 2015, which is incorporated herein by reference.

TECHNICAL FIELD

The technical field relates to a polyphenylene ether oligomer and a high-frequency copper clad laminate.

BACKGROUND

The electronic communications industry has grown rapidly, and the development of a polymer with high thermal resistance, a low dielectric coefficient, and high toughness is desired so that these materials can be used in next-generation electronic packages or high-frequency substrates. Polyphenylene ether (PPE) is a high-performance material. However, the solubility of polyphenylene ether in organic solvent is low, resulting in the range of potential applications for polyphenylene ether materials being limited.

Hence, the development of novel polyphenylene ether materials is desired.

SUMMARY

Embodiments of the disclosure provide a polyphenylene ether oligomer. The polyphenylene ether oligomer has a structure represented by Formula (I):

Formula (I)

wherein each $R^1$ is independently hydrogen, $C_{1-6}$ alkyl or phenyl group; each $R^2$ is independently hydrogen, $C_{1-6}$ alkyl or phenyl group; a:(a+b) is from 0.05:1 to 1:1; n:(a+b) is from 0.05:1 to 5:1; Q is

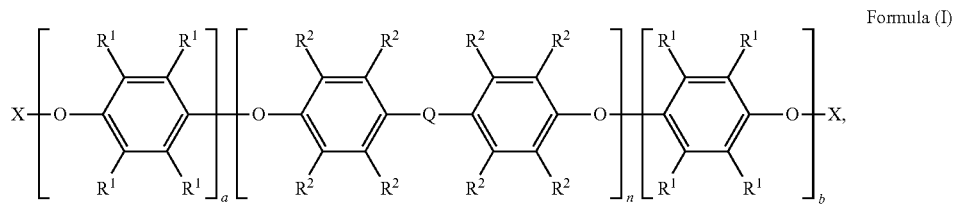

$m$ is 0 or an integer from 1 to 4; Ra is $C_{1-6}$ alkylene group; Rb is $C_{1-6}$ alkylene group; each X is independently hydrogen, acryloyl group, allyl group, vinylbenzyl group, epoxypropyl group, methacryloyl group, propargyl group or cyanol group; and the polyphenylene ether oligomer has a number average molecular weight from 400 to 2,000.

Embodiments of the disclosure provide a high-frequency copper clad laminate. The high-frequency copper clad laminate includes a copper clad laminate and an adhesive layer. The adhesive layer is disposed on the copper clad laminate, wherein the adhesive layer is made from a composition. In particular, the composition includes the aforementioned polyphenylene ether oligomer.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

The polyphenylene ether oligomer of the disclosure exhibits high solubility and good processability, and the product made from the polyphenylene ether oligomer exhibits superior electrical properties.

The disclosure provides a polyphenylene ether oligomer having a Formula (I)

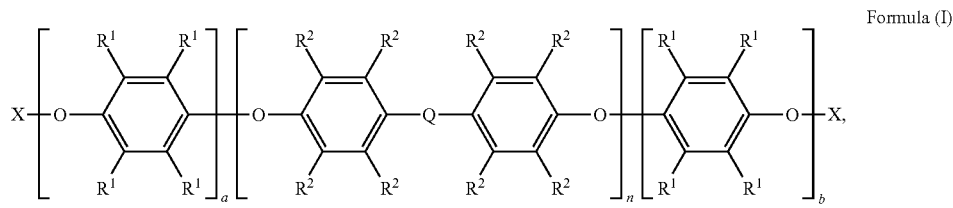

wherein each $R^1$ can be independently hydrogen, $C_{1-6}$ alkyl group, or phenyl group; each $R^2$ can be independently hydrogen, $C_{1-6}$ alkyl group, or phenyl group; a:(a+b) can be from 0.05:1 to 1:1; n:(a+b) can be from 0.05:1 to 5:1.

Q can be

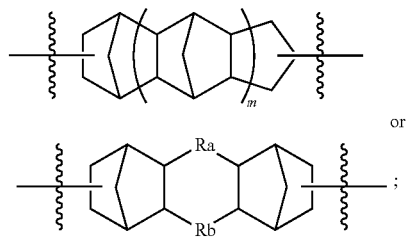

m can be 0, or an integer from 1 to 4; Ra can be $C_{1-6}$ alkylene group; Rb can be $C_{1-6}$ alkylene group; each X can be independently hydrogen, acryloyl group, allyl group, vinylbenzyl group, epoxypropyl group, methacryloyl group, propargyl group, or cyanol group.

In an embodiment of the disclosure, the polyphenylene ether oligomer can have a number average molecular weight from about 400 to 2,000, such as from 500 to 2,000, from 800 to 2,000, from 1,000 to 2,000, or from 900 to 1,700. When the number average molecular weight of the polyphenylene ether oligomer is too low, the polyphenylene ether oligomer will exhibit relatively low thermal stability. When the number average molecular weight of the polyphenylene ether oligomer is too high, the polyphenylene ether oligomer will exhibit relatively poor processability.

It should be noted that the term "a value is from A to B" means the value range is including A and B. For example, the polyphenylene ether oligomer can have a number average molecular weight from 500 to 2000, and the number average molecular weight of the polyphenylene ether oligomer can be 500 or 2000.

In an embodiment of the disclosure, Q can be

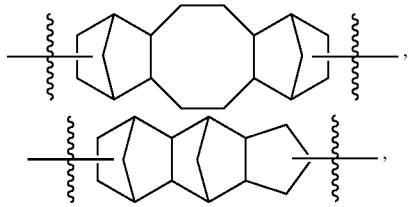

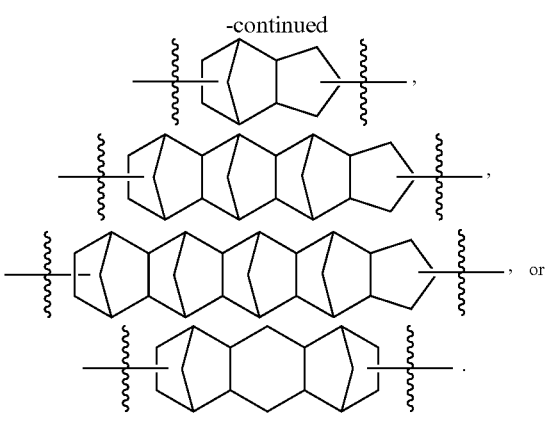

In an embodiment of the disclosure, each X can be independently hydrogen,

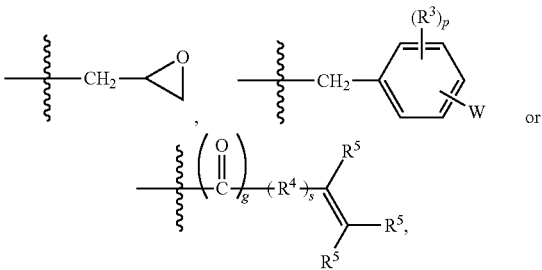

wherein $R^3$ is independently hydrogen or $C_{1-3}$ alkyl group; p is an integer from 1 to 4; W is epoxy group, hydroxyl group, or vinyl group; $R^4$ is $C_{1-12}$ alkylene group; g is 0 or 1; s is 0 or 1; and $R^5$ is independently hydrogen or $C_{1-12}$ alkyl group.

In an embodiment of the disclosure, each X is independently

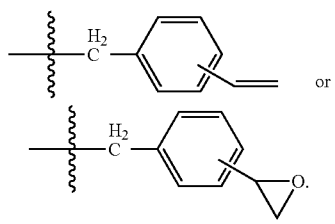

In an embodiment of the disclosure, the polyphenylene ether oligomer can have a structure represented by Formula (II):

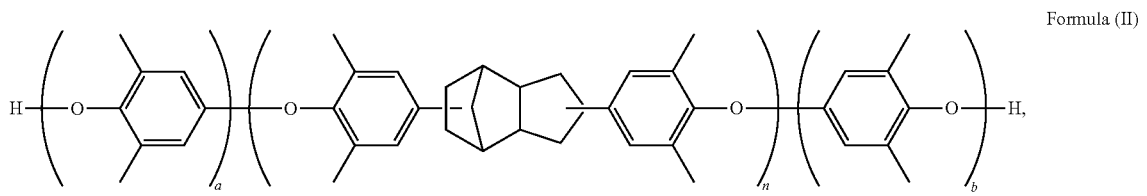

Formula (II)

wherein a:(a+b) is from 0.05:1 to 1:1; and, n:(a+b) is from 0.05:1 to 5:1.

In an embodiment of the disclosure, the polyphenylene ether oligomer can have a structure represented by Formula (III):

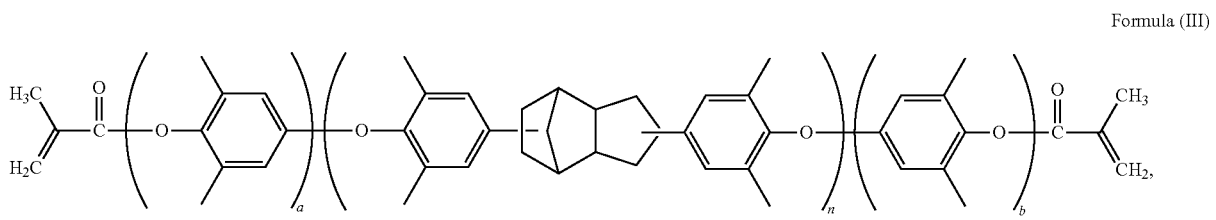

Formula (III)

wherein a:(a+b) is from 0.05:1 to 1:1; and, n:(a+b) is from 0.05:1 to 5:1.

In an embodiment of the disclosure, the polyphenylene ether oligomer can have a structure represented by Formula (IV):

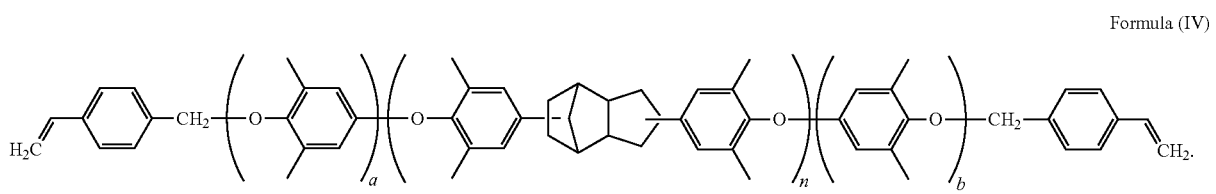

Formula (IV)

wherein a:(a+b) is from 0.05:1 to 1:1; and, n:(a+b) is from 0.05:1 to 5:1.

In an embodiment of the disclosure, the polyphenylene ether oligomer can have a structure represented by Formula (V):

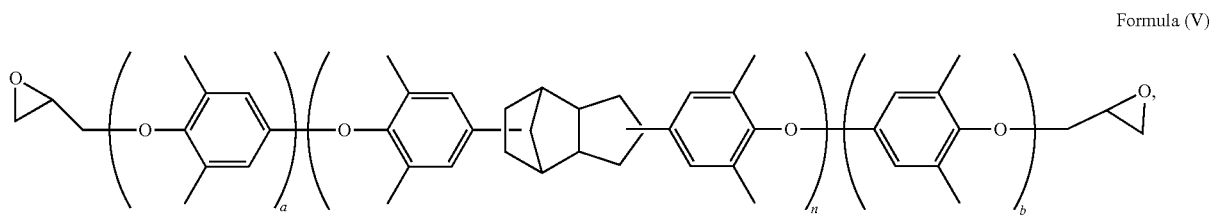

Formula (V)

wherein a:(a+b) is from 0.05:1 to 1:1; and, n:(a+b) is from 0.05:1 to 5:1.

In an embodiment of the disclosure, a bisphenol monomer is prepared from reacting a first reactant (such as

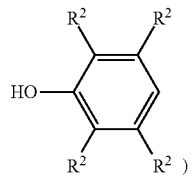

with a second reactant (such as

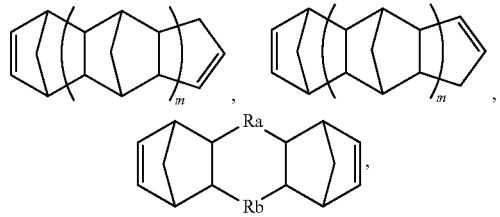

or a combination thereof). Next, the bisphenol monomer is reacted with a third reactant (such as

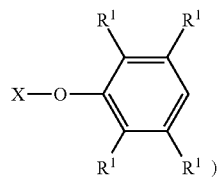

to undergo polymerization, obtaining the polyphenylene ether oligomer. Each $R^1$ is independently hydrogen, $C_{1-6}$ alkyl group, or phenyl group; each $R^2$ is independently hydrogen, $C_{1-6}$ alkyl group, or phenyl group; m is 0 or an integer from 1 to 4; Ra is $C_{1-6}$ alkylene group; Rb is $C_{1-6}$ alkylene group; and, each X is independently hydrogen, acryloyl group, allyl group, vinylbenzyl group, epoxypropyl group, methacryloyl group, propargyl group, or cyanol group.

In an embodiment of the disclosure, the bisphenol monomer is prepared from reacting a first reactant (such as

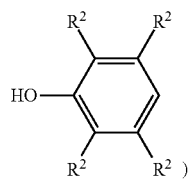

with a second reactant (such as

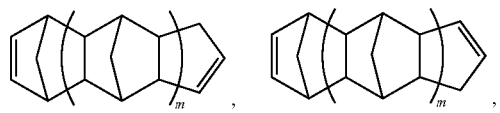

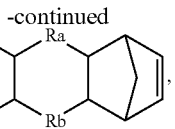

or a combination thereof).

Next, the bisphenol monomer is reacted with a third reactant (such as

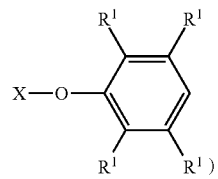

to undergo polymerization, and then the resulting product is reacted with a fourth reactant (such as

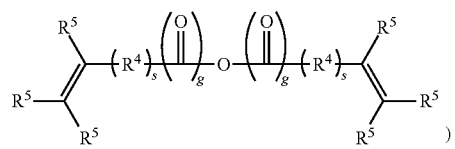

to undergo a substitution reaction, obtaining the polyphenylene ether oligomer.

Each $R^1$ is independently hydrogen, $C_{1-6}$ alkyl group, or phenyl group; each $R^2$ is independently hydrogen, $C_{1-6}$ alkyl group, or phenyl group; m is 0 or an integer from 1 to 4; Ra is $C_{1-6}$ alkylene group; Rb is $C_{1-6}$ alkylene group; each X is independently hydrogen, acryloyl group, allyl group, vinylbenzyl group, epoxypropyl group, methacryloyl group, propargyl group, or cyanol group; $R^4$ is $C_{1-12}$ alkylene group; g is 0 or 1; s is 0 or 1; and $R^5$ is independently hydrogen or $C_{1-12}$ alkyl group.

In an embodiment of the disclosure, the molar ratio between the first reactant (such as

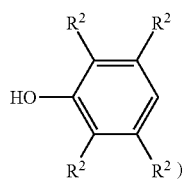

and the second reactant (such as

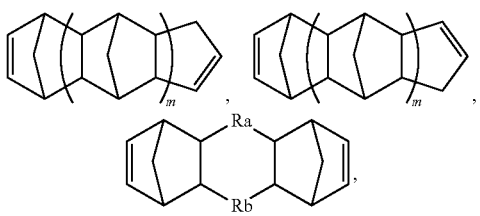

or a combination thereof) is from 2:1 to 3:1.

In an embodiment of the disclosure, the molar ratio between the third reactant (such as

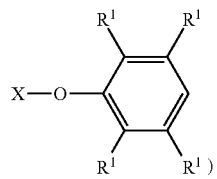

and the second reactant (such as

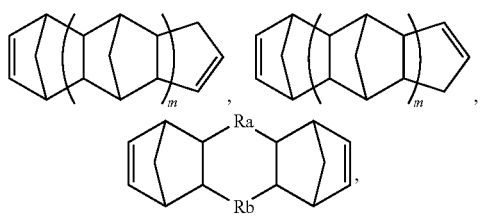

or a combination thereof) is from 0.2:1 to 20:1. When the molar ratio is too low, the polyphenylene ether oligomer will exhibit relatively low thermal stability. When the molar ratio is too high, the polyphenylene ether oligomer will exhibit relatively low toughness.

In an embodiment of the disclosure, the polyphenylene ether oligomer of the disclosure can be used in the process of a high-frequency copper clad laminate. For example, the high-frequency copper clad laminate can include a copper clad laminate and an adhesive layer, wherein the adhesive layer is disposed on the copper clad laminate. The adhesive layer is made from a composition, and wherein the composition comprises the polyphenylene ether oligomer.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1: Preparation of Polyphenylene Ether Oligomer (1)

102.97 g (0.84 mol) of 2,6-dimethylphenol (DMP) and 2.36 g (0.018 mol) of aluminium chloride were added into a reaction bottle, and the reaction bottle was heated to 120° C. under nitrogen atmosphere. Next, 15.6 g (0.12 mol) of dicyclopentadiene was added into the reaction bottle at 120° C. After the reaction was complete, sodium hydroxide (0.06 mol) aqueous solution (5 wt %) was added into the reaction bottle to neutralize the catalyst. Next, toluene was added into the reaction bottle, and then the result was stirred for 1 hr. After removing the salt and catalyst via filtration, the filtrate was collected and washed with water several times, and an organic phase was separated after extraction. After vacuum distillation and purification, 40.61 g of bisphenol monomer (DCPD-DIDMP) (dark brown) was obtained with a yield of 90%.

16.22 g (43.08 mmol) of DCPD-DIDMP, 15.66 g (128.36 mmol) of 2,6-dimethylphenol, 1.33 g (13.14 mmol) of N,N'-dimethylbutylamine, 1.05 g (8.14 mmol) of di-n-butylamine, and 208 g methanol were mixed, obtaining a monomer solution.

0.253 g (1.13 mmol) of copper bromide (CuBr$_2$), 0.71 g (7.02 mmol) of N,N'-dimethylbutylamine, 0.55 g (4.26 mmol) of di-n-butylamine, and 235 g of toulene were added into a reaction bottle. The mixture was stirred under oxygen atmosphere and heated to 45° C. Next, the monomer solution was added into the reaction bottle under oxygen atmosphere.

After the reaction was complete, a solution including 1.2 g (3.16 mmol) of tetrasodium (EDTA) dissolved in 200 g of water was added into the reaction bottle to quench the reaction. After extraction, an organic phase was separated and concentrated, obtaining 28 g of Polyphenylene ether oligomer (1). The synthesis pathway of the above reaction was as follows:

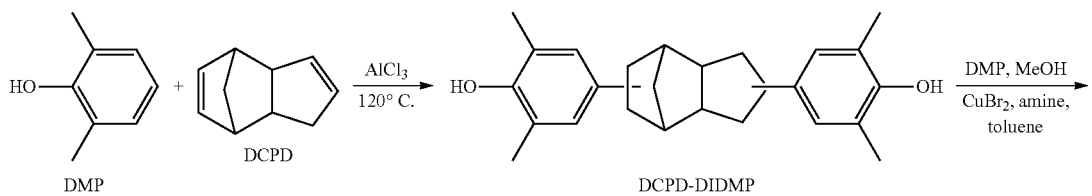

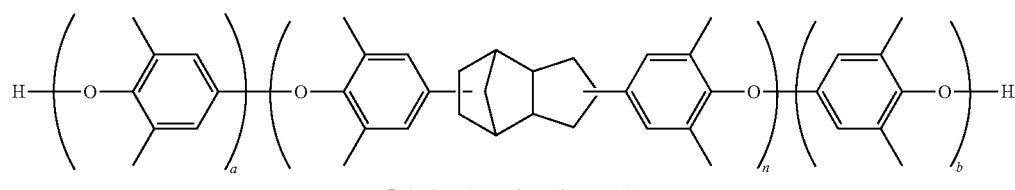

Polyphenylene ether oligomer (1)

(a:(a+b) is from 0.05:1 to 1:1; and n:(a+b) is from 0.05:1 to 5:1)

The physical measurement of DCPD-DIDMP is listed below: $^1$H-NMR (400 MHz, DMSO-d6, δ): 7.93 ppm (—OH), 6.87-6.55 ppm (Aromatic H of DMP), 2.19-1.05 ppm (Aliphatic H of DMP and DCPD). 7.93 ppm signal of chemical shift shows the hydrogen of the phenyl group of DCPD-DIDMP. The physical measurement of Polyphenylene ether oligomer (1) is listed below: $^1$H-NMR (400 MHz, acetone-d6, δ): 7.20-7.15 ppm (5H), 7.09-6.99 ppm (4H), 6.86-6.81 ppm (3H), 6.53-6.50 ppm (2H), 6.34 ppm (1H). The phenolic hydroxyl group of Polyphenylene ether oligomer (1) was confirmed by determining the presence of peak at 3600 cm$^{-1}$ of Fourier-transform infrared (FT-IR) spectroscopy.

The number average molecular weight (Mn) of Polyphenylene ether oligomer (1) was 1,044 and the polydispersity (PDI) of Polyphenylene ether oligomer (1) was about 1.41, which were analyzed by gel permeation chromatography (GPC). Furthermore, the results of the solubility test of Polyphenylene ether oligomer (1) are shown in Table 2.

The solubility test of polyphenylene ether oligomer (1) included the following steps. Polyphenylene ether oligomer (1) and a solvent were mixed to obtain a solution, wherein the weight ratio between Polyphenylene ether oligomer (1) and the solvent was 1:1. Polyphenylene ether oligomer (1) was determined to be soluble in the solvent when the solution was clear without precipitation. In the reverse case, Polyphenylene ether oligomer (1) was determined to be insoluble in the solvent. The solubility test of polyphenylene ether oligomer of the disclosure was performed as described above.

Example 2: Preparation of Polyphenylene Ether Oligomer2

25 g of Polyphenylene ether oligomer (1), 1.17 g (9.58 mmol) of 4-dimethylaminopyridine (DMAP), 16.65 g (107 mmol) of methacrylic anhydride, and 63.8 g of toulene were added into a reaction bottle, and the reaction bottle was heated to 80° C. After the reaction was complete, the reaction bottle was cooled to room temperature, and 63.8 g of toluene was added into the reaction bottle. A sufficient amount of methanol was added into the reaction bottle, and the precipitate was collected by extraction filtration. Next, the precipitate was washed and stirred with 300 ml of methanol for 30 min. After concentrating and drying, 17 g of Polyphenylene ether oligomer (2) was obtained. The synthesis pathway of the above reaction was as follows:

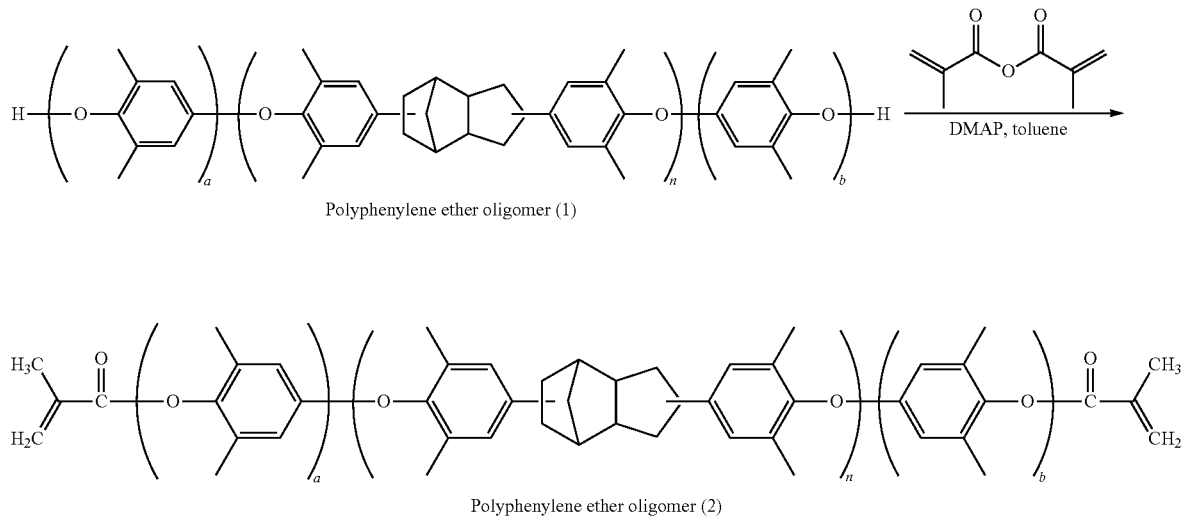

Polyphenylene ether oligomer (1)

Polyphenylene ether oligomer (2)

(a:(a+b) is from 0.05:1 to 1:1; and n:(a+b) is from 0.05:1 to 5:1)

The terminal methacryloyl group of Polyphenylene ether oligomer (2) was confirmed by determining the presence of peak at 1734 cm$^{-1}$ and the absence of peak at 3600 cm$^{-1}$ (phenolic hydroxyl group) of Fourier-transform infrared (FT-IR) spectroscopy. The physical measurement of Polyphenylene ether oligomer (2) is listed below: $^1$H-NMR (400 MHz, acetone-d6, δ): 7.09-6.99 ppm (4H), 6.53-6.48 ppm (3H), 6.33 ppm (2H), 5.83 ppm (1H).

The number average molecular weight (Mn) of Polyphenylene ether oligomer (2) was 1,594 and the polydispersity (PDI) of Polyphenylene ether oligomer (2) was about 1.29, which were analyzed by gel permeation chromatography (GPC). Furthermore, the results of the solubility test of Polyphenylene ether oligomer (2) are shown in Table 2.

Example 3: Preparation of Polyphenylene Ether Oligomer (3)

2 g (1.92 mmol) of Polyphenylene ether oligomer (1) and 20 ml tetrahydrofuran (THF) were added into a reaction bottle, and the reaction bottle was heated to 60° C. under nitrogen atmosphere. Next, 8 g of sodium hydroxide aqueous solution (25 wt %) was added into the reaction bottle. Next, 20 ml (27.5 mmol) of 4-chloromethylstyrene was added into the reaction bottle. After the reaction was complete, the reaction bottle was cooled to room temperature, and the result was extracted by toluene and water. An organic phase was separated and concentrated, and the result was dissolved in toluene and purified by reprecipitation from methanol. After concentrating and drying, 1.2 g of Polyphenylene ether oligomer (3) was obtained. The synthesis pathway of the above reaction was as follows:

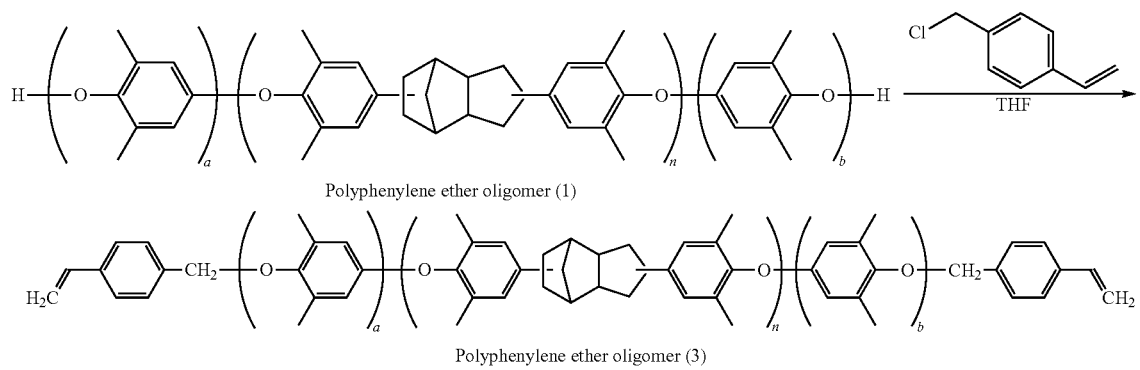

Polyphenylene ether oligomer (1)

Polyphenylene ether oligomer (3)

(a:(a+b) is from 0.05:1 to 1:1; and n:(a+b) is from 0.05:1 to 5:1)

The physical measurement of Polyphenylene ether oligomer (3) is listed below: $^1$H-NMR (400 MHz, CDCl$_3$, δ): 7.44-7.34 ppm (4H), 7.06-6.89 ppm (6H), 6.77-6.73 ppm (2H), 6.47-6.46 ppm (2H), 6.39 ppm (2H), 5.79-5.74 ppm (1H), 5.29-5.25 ppm (1H), 4.76 ppm (2H), 4.58 ppm (1H). The formation of Polyphenylene ether oligomer (3) was confirmed by determining the absence of peak at 3600 cm$^{-1}$ (phenolic hydroxyl group) of Fourier-transform infrared (FT-IR) spectroscopy.

The number average molecular weight (Mn) of Polyphenylene ether oligomer (3) was 1,953 and the polydispersity (PDI) of Polyphenylene ether oligomer (3) was about 1.33, which were analyzed by gel permeation chromatography (GPC).

Example 4: Preparation of Polyphenylene Ether Oligomer (4)

2 g of Polyphenylene ether oligomer (1) (1.92 mmol) and 11.7 g of epichlorohydrin (117 mmol) were added into a reaction bottle, and the reaction bottle was heated to 100° C. under nitrogen atmosphere. Next, 0.36 g of sodium ethoxide (dissolved in 1.6 g of ethanol) was added dropwise into the reaction bottle.

After the reaction was complete, the reaction bottle was cooled to room temperature, and the result was extracted by toluene and water. An organic phase was separated and concentrated, and the resulting product was dissolved in toluene and purified by reprecipitation from methanol. After concentrating and drying, 1.1 g of Polyphenylene ether oligomer (4) was obtained. The synthesis pathway of the above reaction was as follows:

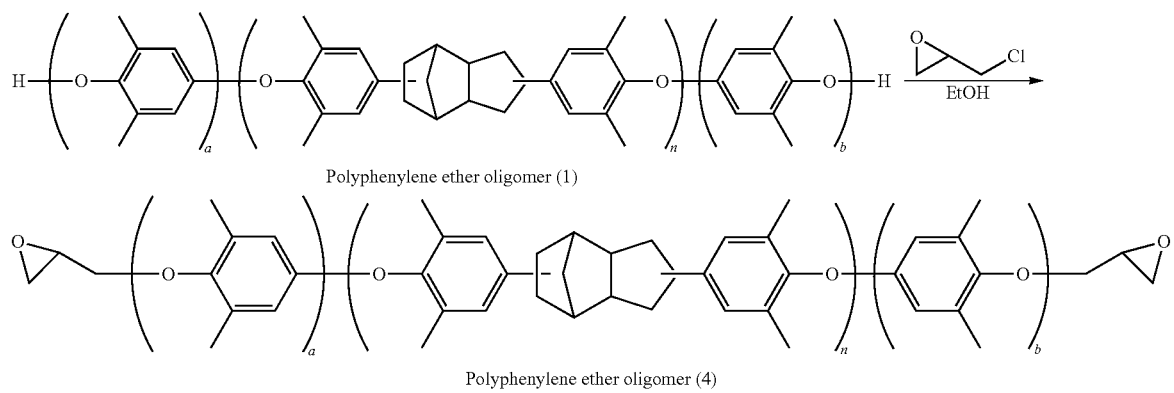

Polyphenylene ether oligomer (1)

Polyphenylene ether oligomer (4)

(a:(a+b) is from 0.05:1 to 1:1; and n:(a+b) is from 0.05:1 to 5:1)

The physical measurement of Polyphenylene ether oligomer (4) is listed below: $^1$H-NMR (400 MHz, acetone-d6, δ): 7.26-7.05 ppm (6H), 6.96-6.91 ppm (2H), 6.54-6.52 ppm (2H), 6.40 ppm (2H), 4.08-4.05 ppm (2H), 3.63-3.59 ppm (1H), 3.30 ppm (2H). The formation of Polyphenylene ether oligomer (4) was confirmed by determining the absence of peak at 3600 cm$^{-1}$ (phenolic hydroxyl group) of Fourier-transform infrared (FT-IR) spectroscopy.

The number average molecular weight (Mn) of Polyphenylene ether oligomer (4) was 1,916 and the polydispersity (PDI) of Polyphenylene ether oligomer (4) was about 1.38, which were analyzed by gel permeation chromatography (GPC).

Example 5: Measurement of Dielectric Properties

A copper clad and an adhesive layer prepared from Polyphenylene ether oligomer (2) were combined via high temperature and pressure lamination process, obtaining a copper clad laminate. Next, the dielectric properties of the copper clad laminate were measured by a dielectric analyzer, and the result is shown in Table 1.

TABLE 1

|  | Dk (5 GHz) | Df (5 GHz) |
|---|---|---|
| Example 5 | 3.94 | 0.004 |

As shown in Table 1, the curing product of the polyphenylene ether oligomer of the disclosure exhibits low dielectric constant (Dk) and dissipation factor (Df).

Comparative Example 1: Preparation of Polyphenylene Ether Oligomer a 16.22 g (43.08 mmol) of DCPD-DIDMP, 52.55 g (430.8 mmol) of 2,6-dimethylphenol, 3.19 g (31.54 mmol) of N,N'-dimethylbutylamine, 2.52 g (19.54 mmol) of di-n-butylamine, and 208 g of methanol were mixed, obtaining a monomer solution.

0.61 g (2.71 mmol) of copper bromide ($CuBr_2$), 1.70 g (16.85 mmol) of N,N'-dimethylbutylamine, 1.32 g (10.22 mmol) of di-n-butylamine, and 235 g of toulene were added into a reaction bottle, and then the reaction bottle was heated to 45° C. under oxygen atmosphere. Next, the monomer solution was added into the reaction bottle under oxygen atmosphere. A solution including 2.88 g (7.58 mmol) of tetrasodium (EDTA) dissolved in 200 g of water was added into the reaction bottle to quench the reaction. After extraction, an organic phase was separated and concentrated, obtaining 62 g of Polyphenylene ether oligomer (A). The number average molecular weight (Mn) of Polyphenylene ether oligomer (A) was 2,009 and the polydispersity (PDI) of Polyphenylene ether oligomer (A) was about 1.54, which were analyzed by gel permeation chromatography (GPC). Furthermore, the results of the solubility test of Polyphenylene ether oligomer (A) are shown in Table 2.

TABLE 2

|  |  |  | Solubility | | |
|---|---|---|---|---|---|
|  | Mn | PDI | toluene (50 wt %) | butanone (50 wt %) | acetone (50 wt %) |
| Polyphenylene ether oligomer (1) (Example 1) | 1,044 | 1.41 | Soluble | Soluble | Soluble |
| Polyphenylene ether oligomer (2) (Example 2) | 1,594 | 1.29 | Soluble | Soluble | Soluble |
| Polyphenylene ether oligomer A (Comparative Example 1) | 2,009 | 1.54 | Soluble | Soluble | Insoluble |

As shown in Table 2, the polyphenylene ether oligomer of the disclosure can be dissolved in various organic solvents (such as acetone) and exhibits good processability.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A polyphenylene ether oligomer, having a structure represented by Formula (I):

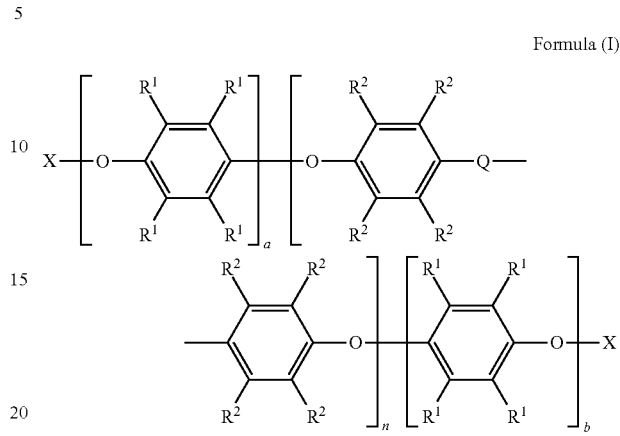

Formula (I)

wherein each $R^1$ is independently hydrogen, $C_{1-6}$ alkyl group, or phenyl group; each $R^2$ is independently hydrogen, $C_{1-6}$ alkyl group, or phenyl group; a:(a+b) is from 0.05:1 to 1:1; n:(a+b) is from 0.05:1 to 5:1; Q is

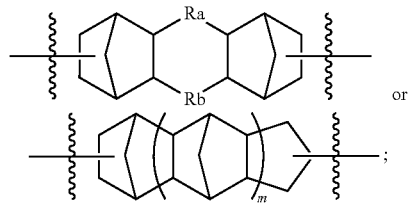

m is 0 or an integer from 1 to 4; Ra is $C_{1-6}$ alkylene group; Rb is $C_{1-6}$ alkylene group; each X is independently hydrogen, acryloyl group, allyl group, vinylbenzyl group, epoxypropyl group, methacryloyl group, propargyl group, or cyanol group; and wherein the polyphenylene ether oligomer has a number average molecular weight from 400 to 2,000.

2. The polyphenylene ether oligomer as claimed in claim 1, wherein Q is

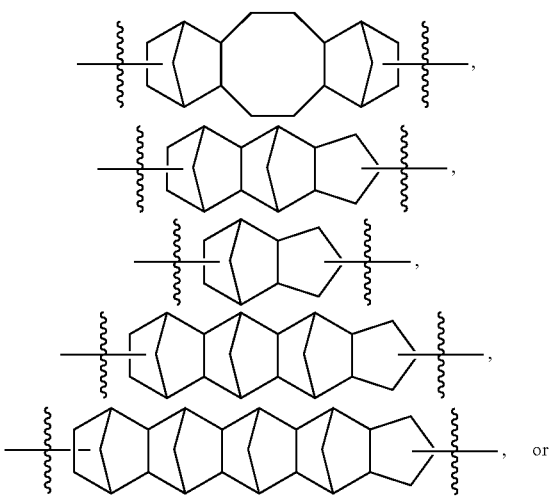

-continued

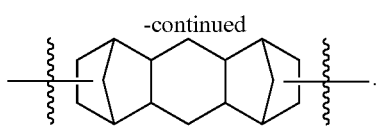

3. The polyphenylene ether oligomer as claimed in claim 1, wherein each X is independently hydrogen,

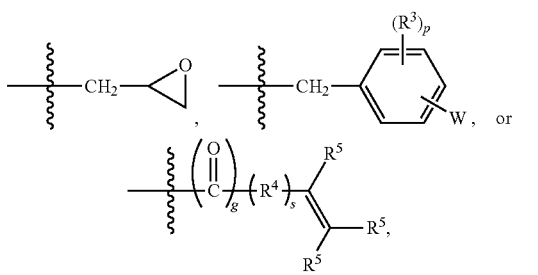

and wherein $R^3$ is independently hydrogen or $C_{1-3}$ alkyl group; p is an integer from 1 to 4; W is epoxy group, hydroxyl group, or vinyl group; $R^4$ is $C_{1-12}$ alkylene group; g is 0 or 1; s is 0 or 1; and $R^5$ is independently hydrogen or $C_{1-12}$ alkyl group.

4. The polyphenylene ether oligomer as claimed in claim 1, wherein each X is independently

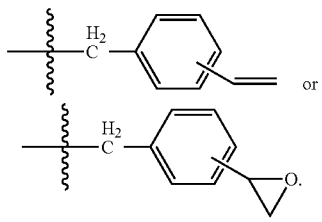

5. The polyphenylene ether oligomer as claimed in claim 1, wherein the polyphenylene ether oligomer has a number average molecular weight from 500 to 2,000.

6. The polyphenylene ether oligomer as claimed in claim 1, wherein the polyphenylene ether oligomer has a structure represented by Formula (II):

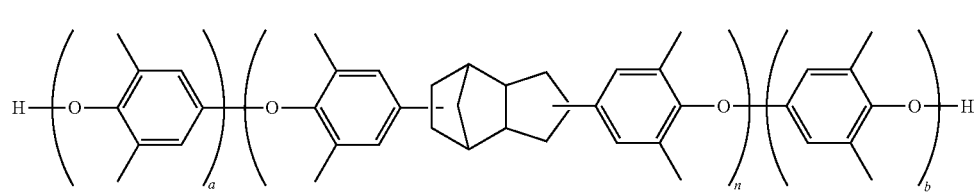

Formula (II)

wherein a:(a+b) is from 0.05:1 to 1:1; n:(a+b) is from 0.05:1 to 5:1.

7. The polyphenylene ether oligomer as claimed in claim 1, wherein the polyphenylene ether oligomer has a structure represented by Formula

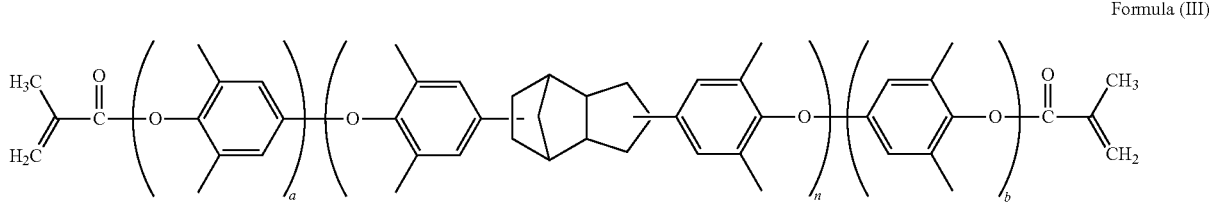

Formula (III)

wherein a:(a+b) is from 0.05:1 to 1:1; n:(a+b) is from 0.05:1 to 5:1.

8. The polyphenylene ether oligomer as claimed in claim 1, wherein the polyphenylene ether oligomer has a structure represented by Formula (IV):

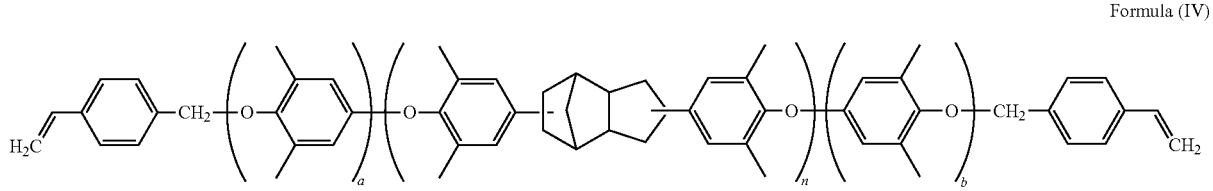

Formula (IV)

wherein a:(a+b) is from 0.05:1 to 1:1; n:(a+b) is from 0.05:1 to 5:1.

9. The polyphenylene ether oligomer as claimed in claim 1, wherein the polyphenylene ether oligomer has a structure represented by Formula (V):

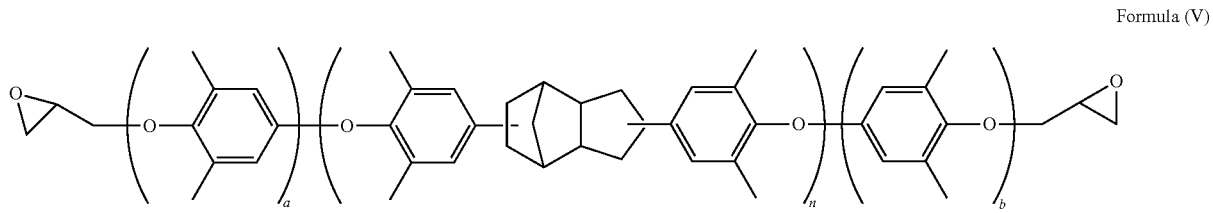

Formula (V)

wherein a:(a+b) is from 0.05:1 to 1:1; n:(a+b) is from 0.05:1 to 5:1.

10. A high-frequency copper clad laminate, comprising:
a copper clad laminate; and
an adhesive layer disposed on the copper clad laminate, wherein the adhesive layer is made from a composition, and wherein the composition comprises the polyphenylene ether oligomer as claimed in claim 1.

* * * * *